(12) United States Patent
Hehli et al.

(10) Patent No.: US 6,730,086 B2
(45) Date of Patent: May 4, 2004

(54) REPOSITIONING INSTRUMENT TO FIXATE BONE-FRACTURES

(75) Inventors: Marcus Hehli, Frauenkirch (CH); Ruedi Ambühl, Filisur (CH); Alberto Fernandez Dell'Oca, Montevideo (UY)

(73) Assignee: Synthes (U.S.A.), Paoli, PA (US)

( * ) Notice: Subject to any disclaimer, the term of this patent is extended or adjusted under 35 U.S.C. 154(b) by 350 days.

(21) Appl. No.: 09/808,947

(22) Filed: Mar. 16, 2001

(65) Prior Publication Data

US 2001/0053911 A1 Dec. 20, 2001

Related U.S. Application Data

(63) Continuation of application No. PCT/CH99/00074, filed on Feb. 16, 1999, and a continuation of application No. PCT/CH98/00399, filed on Sep. 17, 1998.

(51) Int. Cl.$^7$ .............................................. A61B 17/60
(52) U.S. Cl. ......................................... 606/54; 606/205
(58) Field of Search .......................... 606/54, 60, 105, 606/151, 205, 207, 208

(56) References Cited

U.S. PATENT DOCUMENTS

| | | |
|---|---|---|
| 2,631,585 A | 3/1953 | Siebrandt |
| 3,114,367 A | 12/1963 | Carpenter et al. |
| 5,312,403 A | 5/1994 | Frigg ........................... 606/54 |
| 5,578,032 A | * 11/1996 | Lalonde ........................ 606/54 |
| 5,645,548 A | 7/1997 | Augsburger .................. 606/87 |

FOREIGN PATENT DOCUMENTS

| | | |
|---|---|---|
| CH | 607 915 | 11/1976 |
| EP | 0 457 017 A1 | 11/1991 |
| FR | 541 854 | 8/1922 |
| FR | 1 169 404 | 12/1958 |

* cited by examiner

*Primary Examiner*—David O. Reip
(74) *Attorney, Agent, or Firm*—Jones Day

(57) ABSTRACT

The present invention discloses bone grasping tongs for seizing bones or bone fragments. The tongs comprise two mutually pivotable tongs levers fitted with clamping tips at the ends of the tongs levers for seizing the bone. The tongs further comprise a locking element to detachably lock the relative position of the tongs levers and a connecting member to connect with an additional component within an external fixation device. The locking element is located at a distance from the axis of rotation and the longitudinal axis of the connecting member is situated in the plane of pivoting of the tongs lever. The present invention also discloses an external fixation device for externally fixating bone fractures. The device comprises at least one bone grasping tongs, one elongated support, and at least one clamp which detachably connects the connecting member of a bone grasping tongs and an elongated support in a mutually rotatable manner.

16 Claims, 3 Drawing Sheets

REPOSITIONING INSTRUMENT TO FIXATE BONE-FRACTURES

CROSS-REFERENCE TO RELATED APPLICATIONS

This application is a continuation of co-pending International Patent Application PCT/CH99/00074, filed Feb. 16, 1999 and PCT/CH98/00399, filed Sep. 17, 1998, the entire content of which is expressly incorporated herein by reference thereto.

FIELD OF THE INVENTION

The present invention relates to tongs for seizing bones or bone fragments and to a device for external fixation of bone.

BACKGROUND OF THE INVENTION

In addition to conventional external fixation means, which fixate the bones with screws or nails, other devices use bone clamps to fixate bones or bone fragments. The advantages of clamping fixation systems that use bone clamps include: (1) the lower risk of infection otherwise caused by germ invasion along the nails or screws and into the bone; and (2) less interference with blood flow through the bone, such blood flow being substantially hampered when introducing nails or screws.

A device for the fixation of bones or bone fragments is known from published French patent application No. FR 1,169,404 of MONTEZIN. This known device comprises two or more forceps-like instruments to fasten the bone fragments. At the rear end of one of the forceps levers, a rod with teeth is attached such that an additional set of teeth at the rear end of the other forceps lever is engageable and fastenable with the rod to clamp a bone fragment between the tips of the forceps-like instrument. Additionally, a clamp is connected to one of the forceps levers for coupling the instrument with a longitudinal rod by means of a threaded rod and a second clamp. At the longitudinal rod two or several forceps-like instruments are attachable in the same manner. Disadvantages of this design include the decreased stability of the device due to the displaceability and the complicated configuration of the clamps and threaded rod.

A bone clamping forceps for clamping a bone or bone fragment is also known from published Swiss patent application No. CH 607,915 of Sythes AG Chur. This known bone clamping forceps comprises two forceps levers that are fastenable relative to each other by means of a threaded rod. This threaded rod is pivotably connected to one of the forceps levers and is accepted within a bore hole through the other forceps lever. The forceps levers are fastened by means of a nut which is screwable onto the threaded rod. However, this bone clamping forceps lacks any means to connect with another bone clamping forceps. Therefore, additional connection means would have to be attached when required.

European patent application No. 0,457,017 of Synthes AG Chur discloses a clamp fixation system whereby the bone is seized by the tips of bone tongs instead of being gripped by a screw or a nail. This feature offers the advantage that no drilling through the bone is needed, thereby eliminating heat-induced necroses. Furthermore, blood circulation is only minimally impaired. Several such bone tongs can be externally joined together in a way similar to the case of screws and nails. However, the same mechanism used to lock the tongs and to connect several bone tongs together as an external bone fixation device are both configured in the articulation of the bone tongs. This makes the articulation bulky and complex.

Thus, a need exists for improved bone tongs.

SUMMARY OF THE INVENTION

The present invention is directed to simple and manually operable repositioning tongs (or bone grasping tongs) for non-invasive temporary fixation of bone fractures. In addition, two or more of these repositioning tongs can be connected within an external fixation device to fixate bone fractures. In other words, the present invention is directed to both tongs for seizing bone or bone fragments and a device for externally fixating bone fractures.

The repositioning tongs of the present invention comprise two tongs levers joined by a connector or coupler so as to be mutually pivotable about an axis of rotation. The two tongs levers have clamping tips at their ends which serve to seize the bone. Furthermore, a locking means or locking element detachably compresses the tongs levers against each other and locks the tongs levers. Also, a connecting member, such as a connecting bolt, allows the tongs to be connected to another element of an external fixation device. The locking means is located at a first distance from the axis of rotation, whereas the connecting bolt is located at a second distance from the axis of rotation. The longitudinal axis of the connecting bolt is in the plane of pivoting of the tongs levers.

The second distance, which is between the axis of rotation and the connecting bolt, and the first distance, which is between the axis of rotation and the locking means, may be of the same magnitude. Preferably, however, the second distance is smaller than the first distance to preclude large levers between the clamping tips, which seize the bone, and the connecting bolt. Otherwise, large torques might arise in the connecting bolt. On the other hand, the first distance is preferably large so that excessively high stresses in the locking means caused by the clamping force of the repositioning tongs is precluded.

The connecting means pivotably joining the two tongs levers is preferably in the form of a screw threaded into one of the tongs levers and rotatably supported in the other tongs lever. The connecting bolt is cross-sectionally circular-cylindrical.

The locking means is preferably in the form of a tightening screw, which is firmly joined to one of the tongs levers, and a nut which is to be threaded on the screw. By means of an elongated slot, the tightening screw can be displaced in and along the other tongs lever so the levers can be opened and closed. Moreover, the nut may be conically shaped at its end, resting against the tongs lever.

In another embodiment, the locking means may be a clamp moveable into different positions and a serrated rod mounted on the inside of the second tongs lever. The clamp detachably engages the serrations. The serrations are such that, when the tongs levers are forced together, the clamp automatically enters the serrations on the rod. In order to release the locked tongs, the clamp is loosened by hand, namely by switching the clamp into a position at which the serrations at the shaped rod are disengaged.

In another aspect of the present invention, the external fixation device for externally fixating bone fractures comprises at least one repositioning tongs, at least one elongated support, and at least one clamp detachably connecting in mutually rotatable manner the connecting bolt of a repositioning tongs and an elongated support. The clamp consists of two clamp elements mutually rotating about an axis of rotation, each clamp element comprising a continuous cylindrical borehole. These boreholes may be of a circular-cylindrical cross-section corresponding to the cross-section of the connecting bolt and of the elongated support. The axis of rotation about which the two clamps are mutually rotatable is perpendicular to the plane subtended by the two longitudinal axes of the boreholes. By means of a tightening screw, which is concentric with the axis of rotation and which passes through the boreholes in the clamps, the two slotted clamps can each be compressed and can be simultaneously forced against each other. As a result, the connecting bolt of the repositioning tongs is clamped in one clamp and the elongated support is inserted in the borehole of the other clamp. The connecting bolt and the elongated support are thus locked in these clamps. Simultaneously, the mutually rotatable clamps can be affixed in a selected relative position. To better lock the two clamps against rotation, the two abutting end faces of the clamp elements are fitted with mutually engaging serrations.

With the reposition tongs of the present invention, the force exerted by the tongs levers and the position of the repositioning tongs within the external fixation device can be adjusted independently from each other because the connecting bolt is away from the axis of rotation of the repositioning tongs and because the connecting bolt is independent of the locking means. Due to the separation of the connecting means, the locking means, and the axis of rotation, the axis of rotation assumes a simple and compact configuration.

BRIEF DESCRIPTION OF THE DRAWINGS

The present invention is described in detail below with reference to the drawings in which.

DETAILED DESCRIPTION OF PREFERRED EMBODIMENTS

Figure 1:
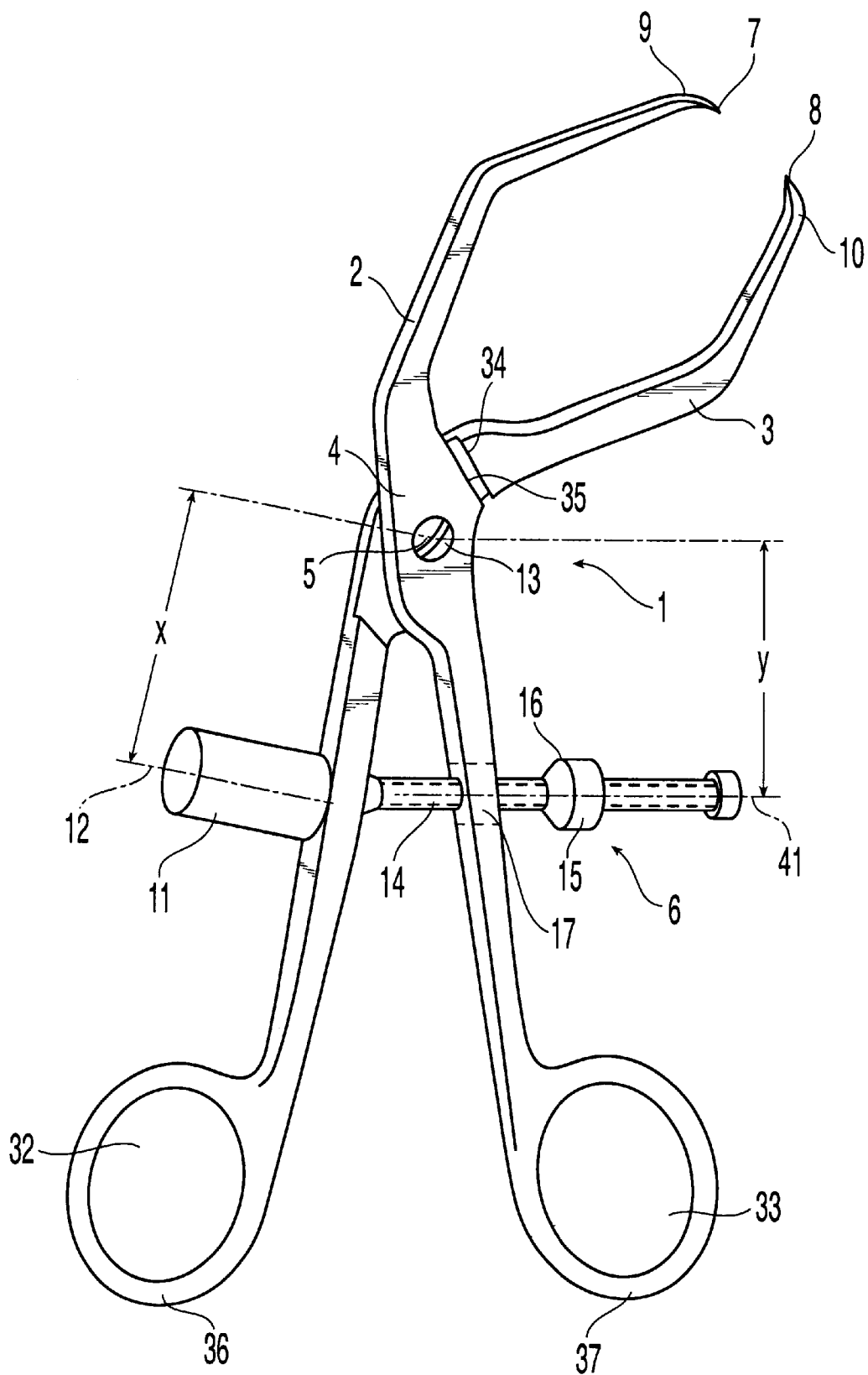
FIG. 1 is a perspective of the repositioning tongs of the present invention.

FIG. 1 shows an embodiment of the repositioning tongs 1 according to the present invention. The tongs comprise two tongs levers 2, 3, which are mutually pivotable about an axis of rotation 5. A rotatable connection or a coupler of the two tongs levers 2, 3 is implemented by a screw 13, which is threaded into a corresponding thread in one of the tongs levers 2, 3 and rotatably supported in the other tongs lever 3, 2. When the tongs levers 2, 3 are spread apart, such an excursion will be limited by stop shoulders 34, 35 present at the levers. Sharp clamping tips 7, 8 are present at the ends 9, 10 of the tongs levers 2, 3 for grasping a bone and the ends 36, 37 are used to operate the repositioning tongs and are fitted with annular finger apertures 32, 33. The repositioning tongs 1 also has a locking means or a locking element 6, which, in the embodiment shown in FIG. 1, consists of a tightening screw 14 affixed to the tongs lever 3 and a nut 15 threading onto the tightening screw 14. The tightening screw 14 is displaceably supported in the tongs lever 2 inside an elongated slot 17 and consequently it will be displaceably along the tongs lever 2 during pivoting motions of the tongs levers 2, 3. The tightening screw 14 and the nut 15 detachably lock the tongs levers 2, 3 in a given position so that the tongs levers 2, 3 will be unable to spread apart farther. In an exemplary embodiment of the repositioning tones, the nut 15 may have an end of conical shape 16. When a bone is clamped between the clamping tips 7, 8, the tightening screw 14 and the nut 15 also maintain a clamping force once the force has been applied. In the embodiment of the repositioning tongs 1 according to the present invention shown here, the tightening screw 14 is mounted a distance y from the axis of rotation 5 toward the ends 36, 37. The repositioning tongs 1 in the embodiment shown also comprise a connecting element 11, such as a connecting bolt, which has a longitudinal axis 12 and a circular-cylindrical cross-section so that the repositioning tongs 1 can be mounted on another component of an external affixation means or an external fixation device. The connecting bolt 11 is mounted at one of the tongs levers 2, 3 at a distance x from the axis of rotation 5 toward the ends 36, 37. The longitudinal axis 12 is located in the plane of pivoting of the tongs levers 2, 3.

Figure 2:
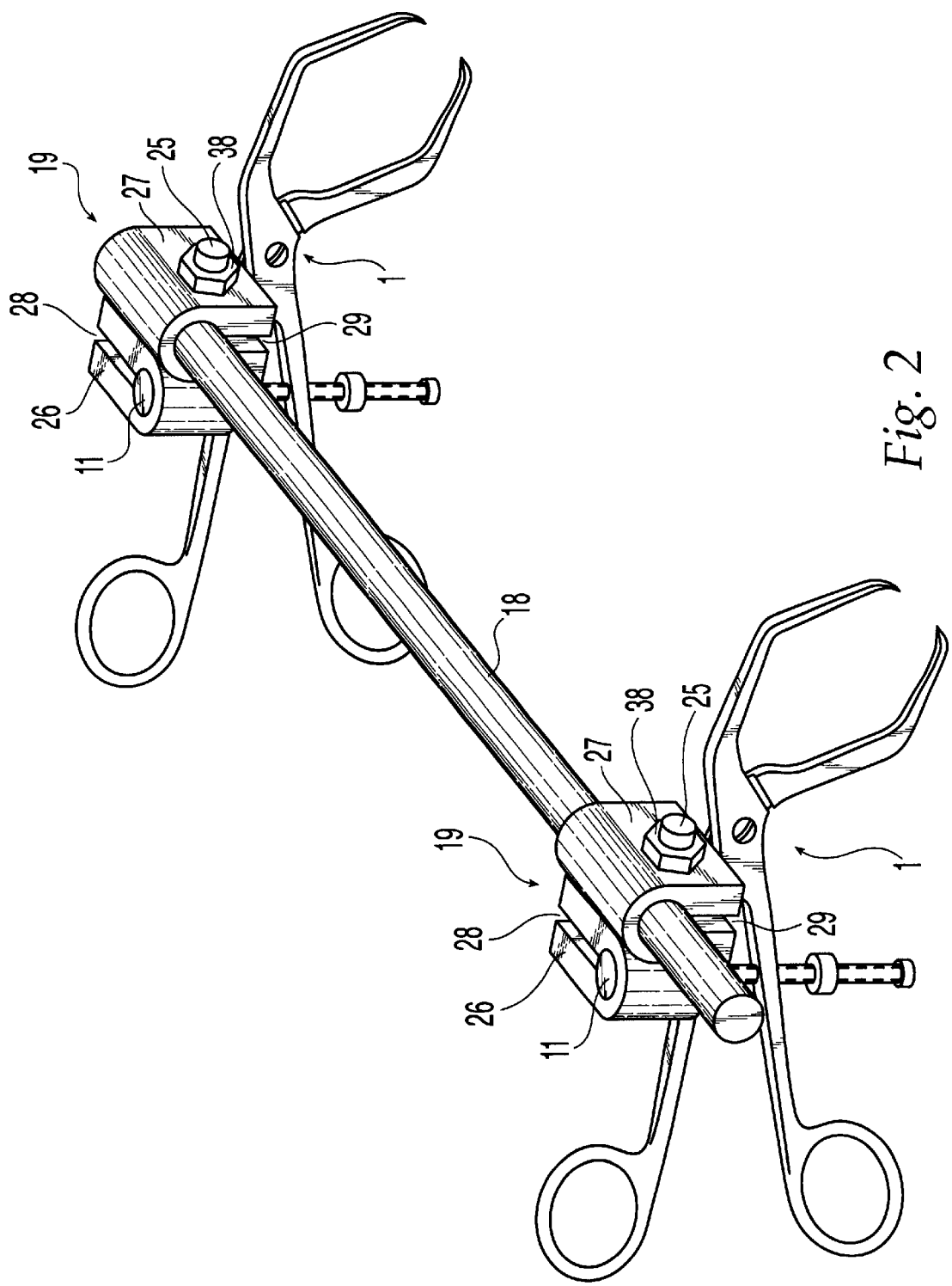
FIG. 2 is a perspective of an illustrative embodiment of the device of the present invention to externally fixate bone fractures.

FIG. 2 shows an embodiment of the external fixation device according to the present invention to externally fixate bone fractures. This device comprises two repositioning tongs such as those shown in FIG. 1, an elongated support 18 to connect the repositioning tongs, and two clamps 19 to attach the repositioning tongs 1 to the elongated support 18. To assemble the present embodiment of the device according to the present invention, the connecting bolts 11, which are each firmly affixed to one lever 2, 3 of each of the two tongs 1, are each inserted into a corresponding borehole in a first clamp element 26 of each of the two clamps 19, and the elongated support 18 is inserted into a second clamp element 27. The connecting bolts 11 and the elongated support 18 are clamped into the boreholes of the clamp elements 26, 27, which are fitted with slots 28, 29, by means of tightening screws 25, which pass through the clamps 19, and by nuts 38, which are screwed onto the threaded ends of the tightening screws 25.

Figure 3:
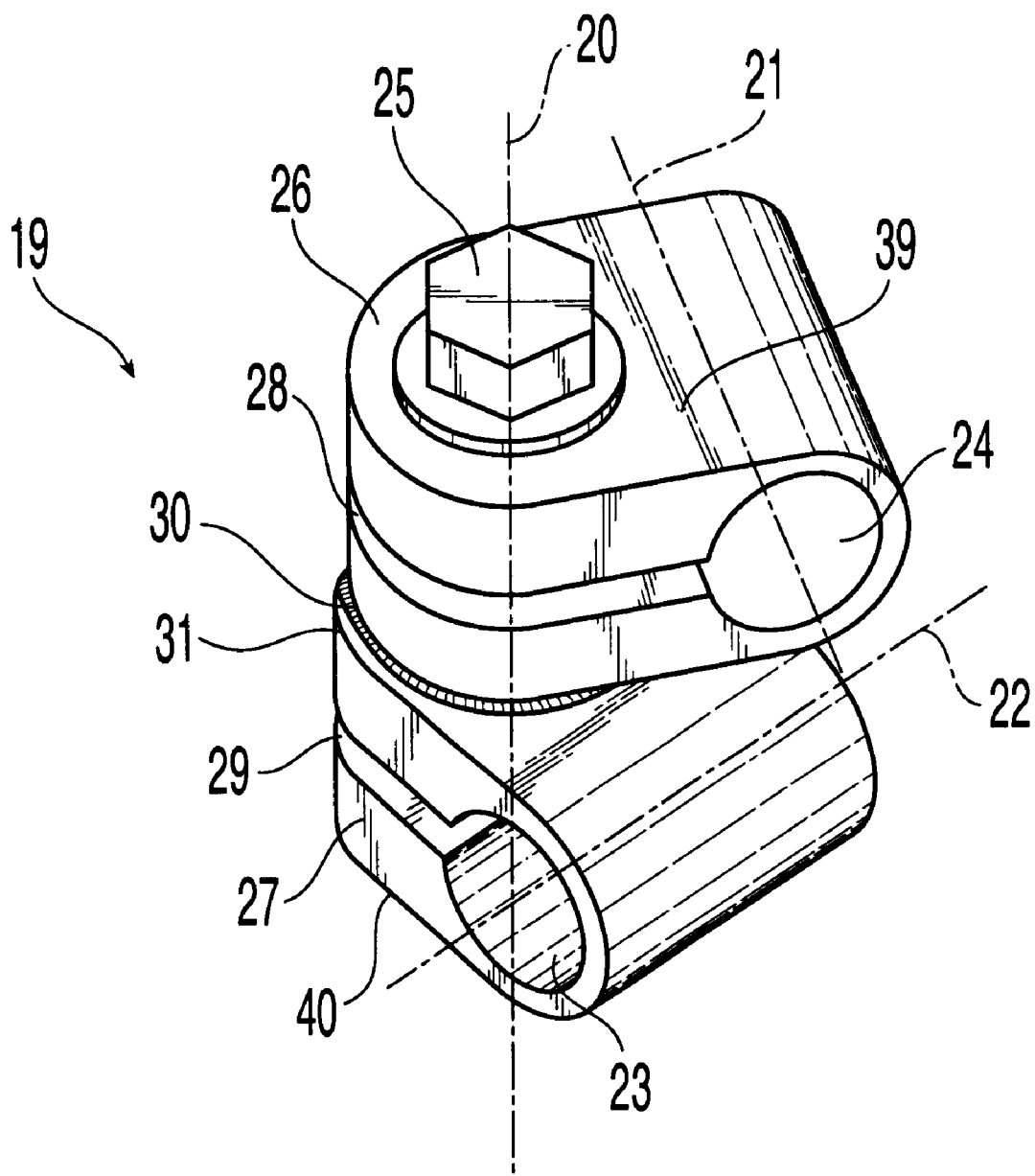
FIG. 3 is a perspective of a clamp of an embodiment of the device of the present invention to externally fixate bone fractures.

FIG. 3 shows an embodiment of a clamp 19, which is part of the external fixation device according to the present invention. The clamp 19 consists of two separate clamp elements 26, 27 crossed by boreholes 23, 24 with longitudinal axes 21 and 22. The end faces 39, 40 of the clamp elements 26, 27 comprise slots 28, 29 running parallel to them and issuing into the boreholes 23, 24. As a result, connecting bolts 11 of the repositioning tongs 1 (see FIGS. 1 and 2) and elongated supports 18 (see FIG. 2) can be affixed in the clamp elements 26, 27 when the latter are being compressed. By tightening a nut 38 (see FIG. 2) which is screwed onto the tightening screw 25 passing through the clamp elements 26, 27 in corresponding continuous boreholes perpendicularly to a plane subtended by the longitudinal axes 21, 22 of the boreholes 23, 24, the clamp elements 26, 27 are compressed and simultaneously forced against each other at their mutually abutting end faces 30, 31. The tightening screw 25 inserted into the boreholes of the clamp elements 26, 27, at the same time, also serves as the axis of rotation 20, as a result of which the two clamp elements will be rotatable by 360° in mutually parallel planes. To achieve improved locking of the entire device of the invention, the mutually abutting end faces 30, 31 of the clamp elements 26, 27 are fitted with mutually engaging serrations.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An external fixation device for external fixation of a bone fracture comprising:
   at least one bone grasping tongs for seizing bone or bone fragments, the at least one bone grasping tongs comprising:
      two tongs levers for seizing a bone,
      a coupler rotatably connecting the two tongs levers to be mutually rotatable about an axis of rotation in a rotation plane,
      a locking element having a longitudinal axis, the tongs levers being detachably fixed with respect to each other by the locking element, and
      a connecting member for operatively coupling the tongs with a bone fixation element, the connecting member having a longitudinal axis and fixed to one of the tongs levers;
   at least one elongated support; and
   at least one clamp, the clamp comprising first and second clamp elements mutually rotatable about an axis of rotation;
   wherein the longitudinal axis of the connecting member is in the rotation plane of the tongs levers and said clamp detachably connects the at least one elongated support and the connecting member of the at least one bone grasping tongs.

2. The external fixation device of claim 1, wherein the elongated support and the connecting member are mutually rotatable with respect to each other.

3. The external fixation device of claim 2, wherein said external fixation device comprises two bone grasping tongs, an elongated support, and first and second clamps, each of the two clamps detachably connecting one bone grasping tongs to the elongated support in a mutually rotating manner.

4. The external fixation device of claim 1, wherein each clamp element is fitted with a continuous cylindrical borehole having a longitudinal axis.

5. The external fixation device of claim 4, wherein the cross-section of the borehole is circular-cylindrical.

6. The external fixation device of claim 4, wherein the axis of rotation of the clamp elements is perpendicular to a plane subtended by the longitudinal axes of the boreholes.

7. The external fixation device of claim 4, wherein each of the clamp elements is fitted with a slot and each of the clamp elements are compressed by a tightening screw passing concentrically with the axis of rotation through the borehole in each of two the clamp elements, and the two clamp elements are forced simultaneously against each other.

8. The external fixation device of claim 1, wherein two mutually abutting end faces of the clamp elements are fitted with mutually engaging serrations.

9. The external fixation device of claim 1, wherein the coupler is a screw threaded into a threaded bore on one of the tongs levers and rotatably supported in the other tongs lever.

10. The external fixation device of claim 1, wherein the longitudinal axis of the locking element is located at a first distance from the axis of rotation; the longitudinal axis of the connecting member is located at a second distance from the axis of rotation; and the second distance is shorter than the first distance.

11. The external fixation device of claim 1, wherein the connecting member is a bolt.

12. The external fixation device of claim 11, wherein the cross-section of the bolt is circular-cylindrical.

13. The external fixation device of claim 1, wherein the locking element comprises a locking screw connected to one of the tongs levers and a nut, and the other tongs lever has an elongated slot with the locking screw displaceable in the elongated slot.

14. The external fixation device of claim 13, wherein the nut has an end configured and dimensioned to rest against one of the tongs levers.

15. The external fixation device of claim 14, wherein the nut comprises a cylindrical shape.

16. An external fixation device, comprising:
   an elongated support;
   at least two bone grasping tongs for seizing bone;
   a locking element extending between said tongs levers, wherein the locking element adjustably secures said tongs levers in a rotation plane;
   a connecting member fixed to one of the tongs levers; wherein the connecting member has a longitudinal axis in the rotation plane of the tongs levers;
   at least two clamps slidably coupled to said elongated support,
   wherein said clamps are slidably and rotatably positionable on said elongated support; and
   each of said two clamps are rotatably coupled to the connecting member of one of said respective bone grasping tongs.

* * * * *